United States Patent [19]

Takashima

[11] 4,200,858
[45] Apr. 29, 1980

[54] ACOUSTIC WAVE SCANNING APPARATUS

[75] Inventor: Matsuo Takashima, Yokohama, Japan

[73] Assignee: Canon Kabushiki Kaisha, Tokyo, Japan

[21] Appl. No.: 913,039

[22] Filed: Jun. 7, 1978

Related U.S. Application Data

[63] Continuation of Ser. No. 758,778, Jan. 12, 1977, abandoned.

[30] Foreign Application Priority Data

Dec. 28, 1976 [JP] Japan .................................. 51-158521

[51] Int. Cl.² .......................... G01S 9/66; G01N 29/00
[52] U.S. Cl. ...................................... 367/135; 73/626; 367/138
[58] Field of Search ................ 73/625, 626; 340/1 R, 340/3 A, 5 R, 5 MP, 3 R

[56] References Cited

U.S. PATENT DOCUMENTS

| | | | |
|---|---|---|---|
| 1,384,029 | 7/1921 | Fessenden | 340/5 R |
| 3,618,006 | 11/1971 | Wright | 340/3 R |
| 3,693,415 | 9/1972 | Waittington | 73/626 |
| 3,820,387 | 6/1974 | Grabendorfer et al. | 73/626 |
| 3,881,466 | 5/1975 | Wilcox | 73/626 |
| 3,919,683 | 11/1975 | Itamura et al. | 73/626 |
| 3,936,791 | 2/1976 | Kossoff | 340/8 L |
| 4,019,169 | 4/1977 | Takamizawa | 73/226 |
| 4,117,446 | 9/1978 | Alais | 73/626 |

Primary Examiner—Anthony V. Ciarlante
Attorney, Agent, or Firm—Fitzpatrick, Cella, Harper & Scinto

[57] ABSTRACT

This specification discloses an apparatus for scanning acoustic waves in accordance with the movement of a presumed axis moving on a certain surface (plane or curved). This apparatus has a multiplicity of acoustic transducer elements arrayed in the direction of movement of the presumed axis (scanning direction). The multiple acoustic transducer elements are grouped into a plurality of sets. At least two of the plurality of sets are associated with, namely, transmit or receive, a predetermined number of wave fronts overlapping one another within a predetermined region of the presumed axis and having their centers of curvature outside the axis as it moves. Thus, there is obtained an effect equivalent to that achieved by throwing thin acoustic beam along the presumed axis or by detecting the acoustic wave at each point on the axis preferentially from the other portions outside of such axis.

18 Claims, 17 Drawing Figures

FIG. 17

ACOUSTIC WAVE SCANNING APPARATUS

This is a continuation of application Ser. No. 758,778 filed Jan. 12, 1977, now abandoned.

BACKGROUND OF THE INVENTION

1. Field of the Invention

This invention relates to an apparatus for scanning acoustic waves.

2. Description of the Prior Art

Acoustic wave scanning is accomplished by causing a acoustic beam always to be around an presumed axis moving on a certain surface which is plane or curved, or by detecting acoustic waves at each point on such axis. Here, the presumed axis means a predetermined direction in which it is expected to obtain information of an object. The movement of the presumed axis may be rotational or translational. Usually, the former is called the sector scan and the latter the linear scan.

The acoustic wave scanning method is classified into the type which comprises rotating or translating a single transducer and the type which uses a transducer element array. The present invention relates to the latter type of method. Therefore, the method using a transducer element array will now be described. For example, the simplest scanning method using a one-dimensional element array is the scanning by successive switching over the array elements. This method, however, has required individual transducer elements to be larger in size in order to reduce the divergence of the acoustic beam. The larger size of the elements has led to greater intervals between acoustic beams, which in turn has led to the disadvantage of a reduced resolving power. To avoid this, there has come into practice a method which comprises subdividing a relatively large transducer element into a plurality of smaller transducer elements and successively displacing the plurality of smaller transducer elements laterally by an amount corresponding to the width a smaller element, thereby effecting the scanning. According to this method, the divergence of the acoustic beam is small as in the previously described method, and the interval between acoustic beams is narrow, so that the resolving power is higher than in the previously described method. Nevertheless, the cross-sectional area of the acoustic beam is large and therefore, this method cannot be adopted where a high resolving power is required. As a remedy to this, there is known the so-called electronic focusing method which comprises imparting an operation time difference distribution to a plurality of the subdivided transducer elements to thereby focus the acoustic wave from said plurality of elements on a point on the presumed axis. This electronic focusing method is highly effective only for the focused point, and on the other portions of the presumed axis the acoustic wave is not focused. Therefore, the resolving power in these portions is not satisfactory.

SUMMARY OF THE INVENTION

It is therefore an object of the present invention to provide an acoustic beam scanning apparatus which can obtain a thin acoustic beam characteristic over a wide range on a presumed axis on a certain surface (plane or curved).

Such an object may be achieved by transmitting or receiving acoustic wave fronts which overlap each other over a certain range on the presumed axis and whose centers of curvature lie outside the presumed axis.

The invention will become more fully apparent from the following detailed description thereof taken in conjunction with the accompanying drawings.

DESCRIPTION OF THE PREFERRED EMBODIMENTS

Figure 1:
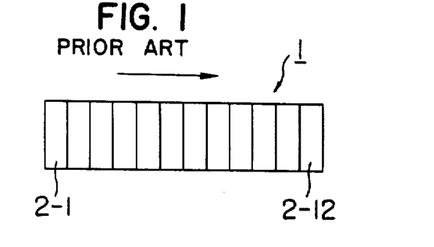
FIG. 1 shows the transducer of the acoustic beam scanning apparatus using a one-dimensional transducer array according to the prior art.

Referring to FIG. 1 which shows the transducer in the acoustic beam scanning device using a one-dimensional transducer array according to the prior art, a transducer array 1 comprises twelve transducer elements 2-1 to 2-12 arrayed in the direction of movement of a presumed axis, namely, in the direction indicated by an arrow. These elements 2-1 to 2-12 are successively operable in such a switch-over fashion that operation of the element 2-1 is followed by operation of the element 2-2. Accordingly, the acoustic beam moves in the direction of movement of the presumed axis. When, however, the operation shifts as from the element 2-1 to the element 2-2, the amount of movement of the acoustic beam corresponds to the width of the element 2 in the direction of arrow. Thus, the resolving power is greatly affected by such width of the element 2. To avoid this, it would occur to mind to reduce the width of the element in the direction of arrow, but reduction in such width would increase the divergence of the acoustic beam in a direction corresponding to the direction of arrow.

Figure 2:
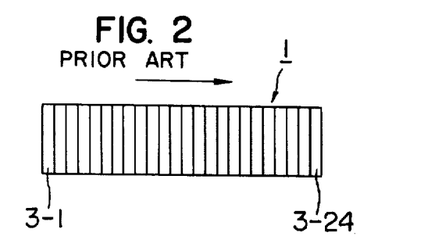
FIG. 2 shows a transducer using subdivided elements arrayed in one dimension.

For this reason, a method has been proposed as shown in FIG. 2, wherein elements 3-1 to 3-24 each having a width reduced by half in the direction of arrow are used and these elements are operated in such a fashion that operation of the elements 3-1, 3-2 is followed by operation of the elements 3-2, 3-3, whereby the amount of movement of the acoustic beam is reduced to a half of that in FIG. 1, thus equalizing the divergence of the beam.

Figure 3:
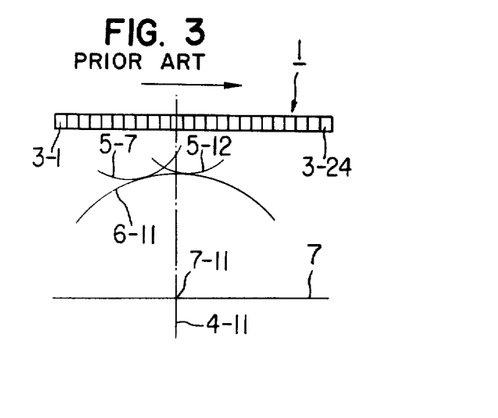
FIG. 3 is a top plan view thereof.

As a method of enhancing the resolving power, there is known the electronic focusing method. FIG. 3 is a top plan view of the transducer 1 comprising twenty-four elements 3-1 to 3-24, and reference numeral 4 designates a presumed axis moving along the plane of the drawing sheet in the direction of arrow. The state of the axis having been moved to the eleventh element is indicated as the axis 4-11. The elements 3 are operated in a pulse-like fashion as the axis 4 moves. Numerals 5-7 to 5-15 indicate the wave fronts of the acoustic waves transmitted from the respective elements 3 when the axis 4 is the axis 4-11. The elements 3 transmit with such a time difference that the envelope 6-11 of these wave fronts 5 has its center of curvature at the point of intersection 7-11 between the axis 4-11 and a scanning line 7. Accordingly, all the acoustic waves 5-7 to 5-15 reach the point 7-11 simultaneously and thus, there occurs such a state as if the acoustic waves from 3-7 to 3-15 were focused on the point 7-11. When the axis has been moved to the twelfth position, the elements 3-8 to 3-16 are controlled so that the envelope is centered at a point 7-12. Thus, as the axis 4 moves, the crossing point of the scanning line 7 and the axis 4 is moved to scan over the scanning line 7. In the case of reception of acoustic wave, entirely conversely of the case of transmission, the reception signal received by the elements 3-7 to 3-15 are added together with a delay imparted to each of them, whereby the acoustic information on the point 7-11 may be detected. Such an acoustic beam scanner is advantageous in detecting the acoustic information on the scanning line 7, inasmuch as the acoustic waves are focused on a point on the axis 4-1, . . . , 4-24, namely, the point 7-1, . . . , 7-24. However, in order to obtain the acoustic information on each point in a certain region on the moving axis, this scanner is disadvantageous in that the receiving characteristics of acoustic wave varies greatly over the region of the axis.

The present invention has been made with such point taken into account. The invention will now be described in conjunction with the drawings.

Figure 4:
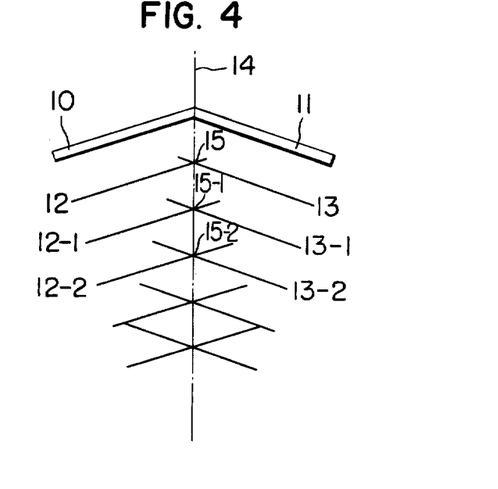
FIG. 4 illustrates the principle of the present invention.

FIG. 4 illustrates the principle of the present invention. Designated by 10 and 11 are transducer elements intersecting each other at an angle therebetween. Plane waves 12 and 13 are transmitted from these transducer elements 10 and 12 simultaneously. The plane waves progress at a predetermined velocity, in the manner as shown by 12-1, 12-2, . . . and 13-1, 13-2 . . . . These waves 12 and 13 overlap each other on a bisecting line 14 and interfere with each other at the point of overlap 15. Thus, the acoustic characteristics in a cross-section containing the points of overlap 15 and perpendicular to the plane of the drawing sheet exhibits a sharp peak of intensity. Then, the point of overlap 15 moves on the bisecting line 14 as the wave; 12 and 13 progress. Thus, there occurs such a state as if thin acoustic beam was thrown along the bisecting line.

In the case of reception, the waves 12 and 13 moving toward the transducer elements 10 and 11 are detected and the detection signals are superposed upon each other, whereby the acoustic information from each point on the bisecting line 14 is more intensely received than that from the other points.

Thus, either by causing a predetermined number of acoustic wave fronts at each point on a certain axis or by detecting a predetermined number of overlapped acoustic wave fronts, there are realized the acoustic transducer which give a less variation in their characteristics along and on the predetermined axis.

In order to provide such characteristics to a transducer, an overlapping predetermined number of acoustic wave fronts to be transmitted or received at each point on the axis, may be such that the centers of curvature thereof lie outside said certain axis. Also the wave fronts may be planar, then the centers of curvature may lie outside of said certain axis at infinity.

When the acoustic beam is scanned, the transducer elements 10 and 11 of FIG. 4 may be either translated or rotated such that the axis is either translated or rotated about a point. However, the method with the mechanical movement of the transducer may not give the high-speed scanning of acoustic beam.

By way of further explanation, it will be seen that the acoustic beam is generated pulsingly from the transducers 10 and 11, in the manner similar to the case of FIG. 3. FIG. 4 is a side view of the transmitting-receiving device consisting of two arrays of the transducer elements which are arranged in the direction perpendicular to the drawing, and the two arrays are angularly combined. It is now assumed that the transducer elements 10 and the transducer elements 11 and all the same in their thickness and their structure of electrode. When the same signals are applied to these elements 10 and 11 simultaneously, two plane waves 12 and 13 of the same frequency are produced from the respective arrays of the transducer elements. The wave front 12 of the waves are in parallel with the surface of the element 10. The direction of the propagation of the wave front is perpendicular to the surface of the element 10. The plane wave 13 is propogated in the direction perpendicular to the surface of the element 11. Since the two plane waves are coherent, they interfere with each other to strengthen or weaken each other. Line 14 is a bisector of the angle formed by the surfaces of the transducer elements 10 and 12. So, if lines are drawn from a point on this bisector line to the surfaces of the two transducer elements, perpendicularly thereto, the length of the perpendicular lines are equal to each other. Since the directions of these perpendicular lines are equal to the directions of the propagations of the plane waves 12 and 13, the two plane waves from the transducer elements 10 and 11 reach the bisector line 14 substantially simultaneously, if the speed of sound of the propagation medium is substantially uniform. This means that the two plane waves reach there in the same phase, thus the two plane waves 12 and 13 strengthen each other. Since the perpendicular lines are equal to each other at any given point on the bisector line 14, the plane waves strengthen each other at any point on the line 14.

As pointed out above, the present invention employs a pulse wave. Therefore, the waves designated by reference numerals 12 and 13 (FIG. 4) are pulse plane waves. The lines 12 and 13 themselves show the center of the pulse waves. Since the pulse waves are used, the point where the two waves strengthen each other, moves on the line 14 in the direction away from the transducer elements, with elapse of the time. For example, the pulse plane waves are generated by the transducer elements 10 and 11. When time tO elapses therefrom, the center of the wave fronts are superposed at a point 15 on the line 14; and at this point of the time, the waves are strengthened only at the area adjacent to the point 15. At the other areas, there exists no strengthening wave, since the acoustic wave is not a continuous one. After the time 2tO elapses, the two waves strengthen each other at point 15-1 on the line 14. Similarly, when the time 3tO elapses after the generation of the two plane waves, they strengthen each other at point 15-2 which is also on line 14. Thus, the area where the two waves strengthen each other travels on the line 14 away from the transducer with the propagation of the waves, as time elapses.

The foregoing description was about the strengthening of the waves. We will discuss in more detail the area where the waves strengthen each other, especially about why the waves strengthen each other only on and adjacent to the line 14.

When time 3tO elapses from the generation of the two waves, the centers of the two pulse waves are on 12-2 and 13-2. At that time, these centers are superposed at a point 15-2 on line 14 where the two waves strengthen each other. At instant point of this time (3tO), the area where the acoustic wave exists is limited to the area around 12-2 and 13-2 within the length of a half of the pulse width therefrom (more specifically, the perpendicular length obtained by multiplying the speed of sound by the time period corresponding to a half of the pulse width). For these reasons, there exists no strengthening wave, at that instant, at any point which is remote from point 15-2 and which is in the plane perpendicular to line 14 and including the point 15-2. Even within the area nearer than said any point, the existing waves do not always interfere with each other since the phases can be different. In addition, on the occasion that the pulse wave is not such an exact rectangular form, but is such an exponential form which goes down gradually at the ends thereof, the degree of the strengthening is weaker than at the point 15-2. Accordingly, in the plane perpendicular to the line 14, the area where the waves are strengthened is limited to on and adjacent to the line 14.

In other words, the waves generated by the transducer elements 10 and 11, form strengthened sound field locally at point 15-2 on line 14, when time 3tO elapses from the generation of the waves. At that time, there is the sound field at the other space around 12-2 and 13-2. However, as discussed above, the latter sound field is not stronger than that at 15-2.

If it assumed that there is a very small item at the position of 15-2, which scatters the acoustic waves, the scattered waves are then received by the transducer elements 10 and 11 simultaneously and then produce a signal by combining the received signals. The characteristics of the combined signal is such that it is more sensitive when the item is placed at 15-2 than when it is placed elsewhere in the plane perpendicular to line 14 and including point 15-2. The overall transmitting-receiving characteristics of the transmitting-receiving device comprising the transducer elements 10 and 11 as shown in FIG. 4 are generally proportional to a square of the sound field at the time of transmission. Therefore, the characteristics are best on the line 14 among any given points on a plane perpendicular to the line 14. Thus, the local area of the best characteristic is established.

Generally speaking, there is a system wherein a transducer has its spherical surface to generate a spherical wave converging at the center of the curvature of the spherical surface, in order to improve the resolving power in the direction from the transducer to the scanning line, that is the direction of the presumed line. Although the high resolving power results at the area, the distance from which is generally equal to the radius of the curvature, because of the converging of the waves, the resolving power is lower at the area before and beyond the area. In other words, the depth of focus, as used in the photographic field, is shorter.

According to the present invention, as embodied in FIG. 4, two plane waves are superposed to strengthen each other, and the strengthened area travels on line 14 with elapse of time, thus achieving an array projection system which is characterized by a long depth of focus, that is, better resolving power in the direction of the presumed line.

Figure 5:
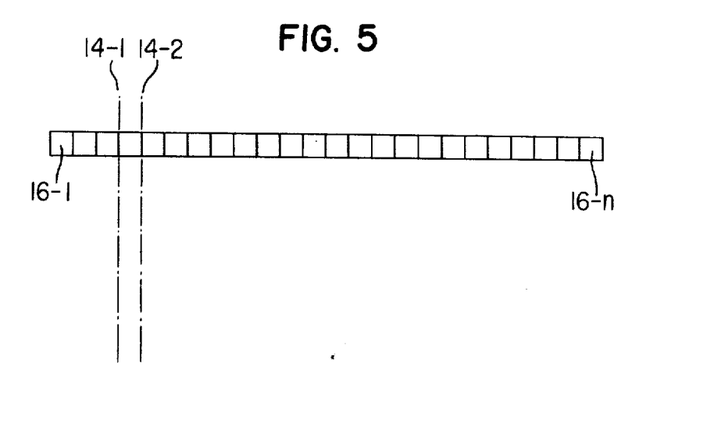
FIG. 5 shows a first embodiment of the present invention.

FIG. 5 shows an embodiment of the present invention which may accomplish high-speed scanning without translating or rotating the transducers.

In this embodiment, a number of transducer elements are selectively operated group by group in succession, as in FIG. 2. More specifically, the transducer elements are operated in such a manner that operation of the group including elements 16-1, 16-2, . . . , 16-5, 16-6 is followed by operation of the group including elements 16-2, 16-3, . . . , 16-6, 16-7. Also, a delay is imparted to the operation of each element so that the set of the first, second and third elements in each group creates the wave front 12 shown in FIG. 4 and the set of the fourth, fifth and sixth elements in each group creates the wave front 13 shown in FIG. 13. Accordingly, the two wave fronts from the elements in the first group overlap each other on a presumed axis 14-1 and the two wave fronts from the elements in the second group overlap each other on the axis 14-2. Thus, by the groups being successively switched over, there can be provided such a state as if the centers of curvature of the two wave fronts and the presumed axis 14 were translated in the direction of switching-over, thus enabling acoustic beam scanning.

Figure 6:
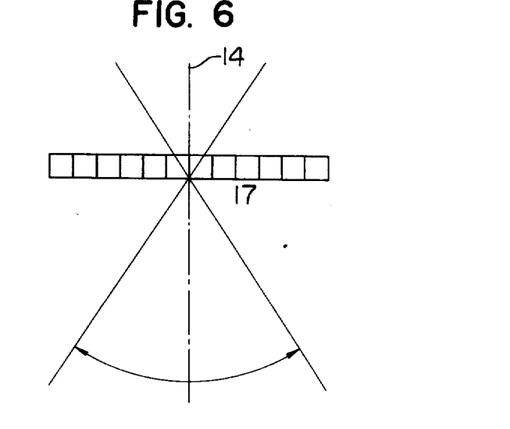
FIG. 6 shows a second embodiment of the present invention.

To effect sector scan, the presumed axis 14 may be oscillated about the point 17 as shown in FIG. 6 to thereby cause the wave front from the right half of the transducer and the wave front from the left half of the transducer to overlap each other on the presumed axis.

In the first and second embodiment described above, the two wave fronts are overlapped with each other and such overlap of the two wave fronts results in sheet-like beam scanning. To avoid this, three dimensional overlap of wave fronts becomes necessary.

Further explaining the embodiment of FIG. 5, the transducer elements are designated by 16-n (n: Integer), with the first one being 16-1. The transmitting group consists of six elements. In the first group actuation, the group consists of the elements 16-1 to 16-6, and the center, that is, the presumed axis 14-1 is at the center of the group, that is, between the element 16-3 and element 16-4. In the second group actuation, the group consists of the elements 16-2 to 16-7, and the presumed axis is as shown by phantom line 14-2. Similarly, the group is gradually sequentially changed to move the presumed line by the amount of the width of the element at a time. As a result, the scanning operation is carried out in the direction parallel to the line of the transducer elements.

Next, the description will be made about the correspondence between the acoustic wave transmitting systems of FIG. 4 and FIG. 5. The element 10 of FIG. 4 corresponds to the sub-group of the elements 16-1, 16-2 and 16-3 of FIG. 5, in the case of the first group acutation of FIG. 5. The element 11 of FIG. 4 corresponds to the sub-group consisting of the elements 16-4, 16-5 and 16-6. The important point is that the elements 16-1, 16-2 and 16-3 are actuated subsequently so as to form a wave front comparable to the wave front 12 of FIG. 4. Similarly, the elements 16-4, 16-5 and 16-6 are actuated with proper timings so as to form a wave front comparable to the wave front 13 of FIG. 4. This is the description of the first group actuation. At the second actuation, elements 16-2, 16-3, 16-4 are actuated similarly, that is, so as to form a wave front corresponding to the wave front 12; and elements 16-5, 16-6 and 16-7 are actuated similarly, that is, so as to form a wave front corresponding to the wave front 13.

Figure 7:
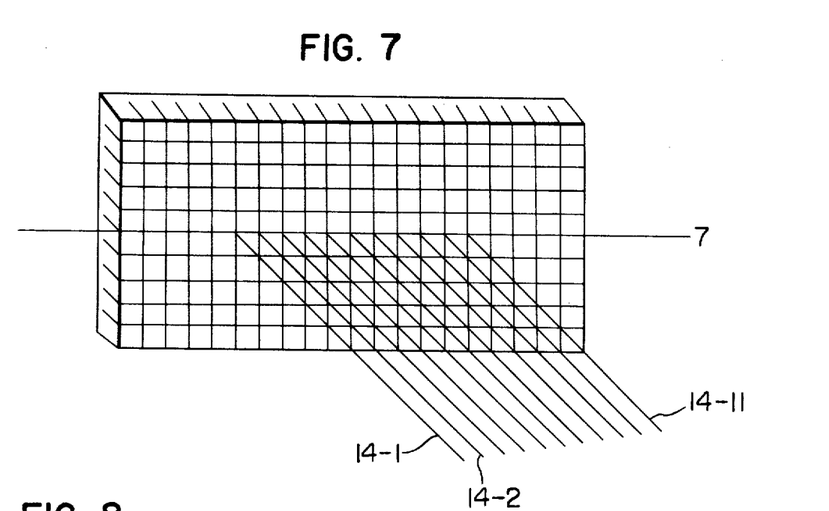
FIG. 7 shows a third embodiment of the present invention.
Figure 8:
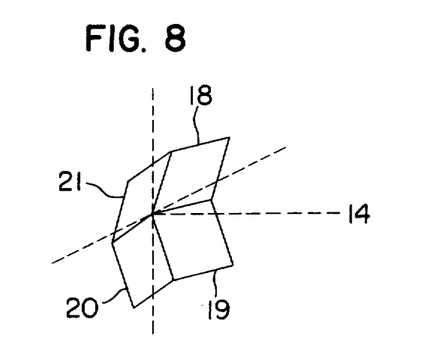
FIGS. 8 to 15 show further embodiments of the present invention.
Figure 14:
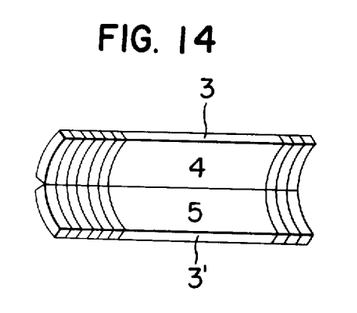

In the third embodiment, illustrated in FIG. 7, transducer elements are arrayed two-dimensionally. When the presumed axis 14 is situated at the position 14-1, the transducer elements in the first to the tenth columns are operated and when the presumed axis 14 is situated at In the case of the transmission, it is divided into four groups each consisting of 5×5 element array, as follows:

$$\begin{pmatrix} 1\text{-}1 & \cdots & 1\text{-}5 \\ \cdot & & \cdot \\ \cdot & & \cdot \\ 5\text{-}1 & \cdots & 5\text{-}5 \end{pmatrix} \begin{pmatrix} 1\text{-}6 & \cdots & 1\text{-}10 \\ \cdot & & \cdot \\ \cdot & & \cdot \\ 5\text{-}6 & \cdots & 5\text{-}10 \end{pmatrix} \begin{pmatrix} 6\text{-}1 & \cdots & 6\text{-}5 \\ \cdot & & \cdot \\ \cdot & & \cdot \\ 10\text{-}1 & \cdots & 10\text{-}5 \end{pmatrix} \begin{pmatrix} 6\text{-}6 & \cdots & 6\text{-}10 \\ \cdot & & \cdot \\ \cdot & & \cdot \\ 10\text{-}6 & \cdots & 10\text{-}10 \end{pmatrix}$$

the position 14-2, the transducer elements in the second to eleventh columns are operated. The transducers under operation are divided into four groups located symmetrically with respect to the axis 14. The transducer elements in respective groups are actuated with such time difference distributions as to provide four wave fronts 18, 19, 20 and 21 which are overlapped with one another at a point on the axis 14 as shown in FIG. 8. In order to effect the sector scanning in this embodiment, all the transducer elements are actuated so as to oscillate the axis 14 shown in FIG. 14, by giving the time difference distributions to the elements to provide the time difference distributions to the elements to provide four wave fronts 18, 19, 20 and 21 overlapping one another at a point on the oscillating axis 14.

The inclination of the wave fronts in the direction perpendicular to the scanning direction, which is provided by the time difference distribution in the embodiment of FIG. 7, may be achieved by inclining the transducers. By doing so, rather than using the time difference, the control of the transducers is simplified, since it does not require the time difference in that direction.

Further explaining this embodiment, it will be recalled that in the FIG. 5 embodiment, six elements are used in each transmitting-receiving group, whereas the FIG. 6 embodiment uses 10×10 element in each transmitting-receiving group. Assuming that the transmission starts at the left hand side of FIG. 7, the signal is applied to 10×10 matrix of the left side. The central axis of the beam is shown by 14-1, in this instance. Namely, the acoustic beam is propagated in the direction of the presumed axis 14-1. The second actuation is effected to the matrix 10×10 elements which are placed at the position shifted by the amount of one element, thus shifting the presumed axis to 14-2. In this manner, the presumed axis is shifted sequentially by the amount of a single element at a time, thus effecting the scanning operation in the direction.

The explanation will be made more specifically on the first group transmission. At this time, 10×10 are actuated. These 100 elements can be expressed with reference numbers, as follows:

$$\begin{pmatrix} 1\text{-}1, 1\text{-}2 \cdots & 1\text{-}5 & 1\text{-}6, 1\text{-}7 \cdots & 1\text{-}10 \\ 2\text{-}1 \cdots & & & \\ \cdot & \cdot & \cdot & \cdot \\ \cdot & \cdot & \cdot & \cdot \\ \cdot & \cdot & \cdot & \cdot \\ 5\text{-}1 \cdots & 5\text{-}5 & 5\text{-}6 \cdots & 5\text{-}10 \\ \hline 6\text{-}1 \cdots & 6\text{-}5 & 6\text{-}6 \cdots & 6\text{-}10 \\ \cdot & \cdot & \cdot & \cdot \\ \cdot & \cdot & \cdot & \cdot \\ \cdot & \cdot & \cdot & \cdot \\ 10\text{-}1 \cdots & 10\text{-}5 & 10\text{-}6 & 10\text{-}10 \end{pmatrix}$$

The elements of each of these groups are actuated sequentially (with delay) so as to obtain a desired wave front. In this embodiment (FIG. 7) the interference among four envelope surfaces is used, instead of two envelope surfaces as in FIG. 5, and instead of two wave fronts as in FIG. 4 embodiments.

Next, the wave fronts 18, 19, 20 and 21 of FIG. 8 will be explained. Similarly to FIG. 7 embodiment, the acoustic waves are oscillated from four 5×5 element array. In the case of FIG. 8 embodiment, the envelope surface of the wave front is a plane. The wave fronts 18, 19, 20 and 21 correspond in the following manner:

21 ——— the envelope surface of the wave fronts generated by
$$\begin{pmatrix} 1\text{-}1 & \cdots\cdots & 1\text{-}5 \\ \vdots & & \vdots \\ 5\text{-}1 & \cdots\cdots & 5\text{-}5 \end{pmatrix}$$

20 ——— the envelope surface of the wave fronts generated by
$$\begin{pmatrix} 6\text{-}1 & \cdots\cdots & 6\text{-}5 \\ \vdots & & \vdots \\ 10\text{-}1 & \cdots\cdots & 10\text{-}5 \end{pmatrix}$$

18 ——— the envelope surface of the wave fronts generated by
$$\begin{pmatrix} 1\text{-}6 & \cdots\cdots & 1\text{-}10 \\ \vdots & & \vdots \\ 5\text{-}6 & \cdots\cdots & 5\text{-}10 \end{pmatrix}$$

19 ——— the envelope surface of the wave fronts generated by
$$\begin{pmatrix} 6\text{-}6 & \cdots\cdots & 6\text{-}10 \\ \vdots & & \vdots \\ 10\text{-}6 & \cdots\cdots & 10\text{-}10 \end{pmatrix}$$

The fourth embodiment wherein the transducers are arranged in such a manner, will be described in conjunction with FIG. 9. Two rows of transducers 22 and 23 are fixed with the same angle with respect to the plane formed by the axis 14 moved for the scan. In operation, the transducers 24 and 25 in the upper row and the transducers 26 and 27 of the lower row are actuated so that four wave fronts overlap one another at a point on the axis 14. With the movement of the axis 14, these four sets are operated as if they were translated by an amount corresponding to the width of a transducer element in the direction of movement of the axis 14. Thus, with the movement of the axis 14, these four sets of wave fronts are moved as if the centers of curvature outside the axis 14 were moved by an amount corresponding to the amount of movement of the axis 14.

Figure 10:
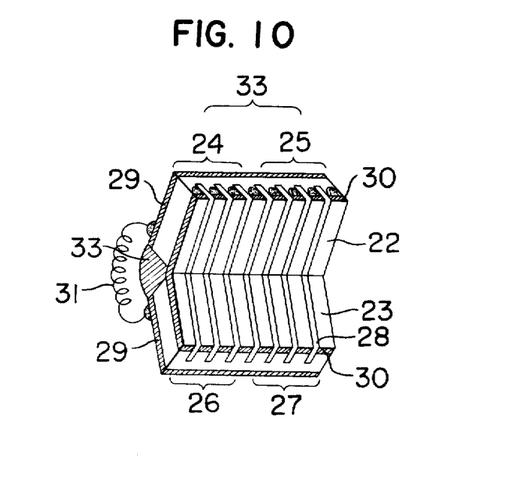

Referring to FIG. 10, there is shown an embodiment in which sector scan is effected by two rows of transducer elements arrayed on an angled plane. Again, the transducer elements in FIG. 10 are divided into four sets and at the oscillation of the moving axis 14, these four sets of transducers are operated as if the wave fronts from the respective sets overlapped on the oscillating axis 14 as shown in FIG. 8.

Figure 9:
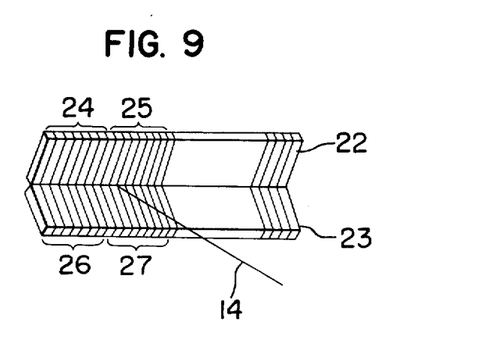

According to the embodiments of FIGS. 9 and 10, the respective rows of transducer elements are arrayed with grooves 28 of a predetermined width provided on a plate of piezoelectric material, and common electrodes 29 are provided on the back surface of the elements and separate electrodes 30 are provided on the front surface of the elements. The common electrodes on the upper 22 and the lower row 23 are electrically connected together by a single lead wire 31. The separate electrodes 30 are also electrically connected together at borderline for each column. The lead wire 31 and the lead wire 32 provided on each of the separating electrodes 30 are connected to an electric control circuit, not shown. Designated by 33 is a bonding agent for securing together the plates 22 and 23 at an angle. Alternatively, a number of small plates of piezoelectric material provided with grooves 28 may be arrayed in the direction of row.

Figure 11:
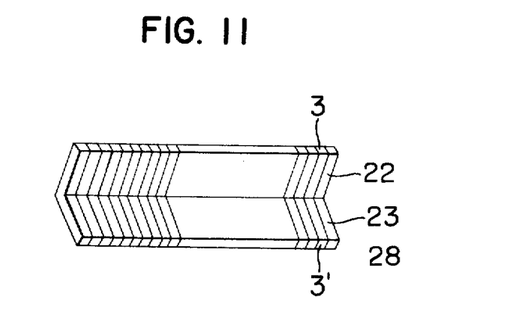

In FIGS. 9 and 10, two plates 22 and 23 are shown as being used, but alternatively, as shown in FIG. 11, the transducer may be provided by forming grooves 28 in a single piezoelectric structure comprising two portions 22 and 23 integrally formed with an angle therebetween. Moreover, the element row of the transducer may be manufactured by joining a plurality of modules each having a plurality of elements.

Figure 12:
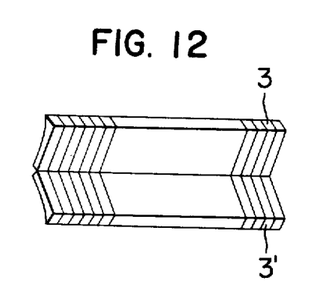

In a further embodiment shown in FIG. 12, each of transducer array 3 and 3' has a thickness distribution which is not uniform in the direction perpendicular to the direction of row of the transducer elements, namely, in the lengthwise direction of the elements. By this, the transmission or reception gain of the respective acoustic waves transmitted or received by the elements may be given a distribution in the lengthwise direction of the elements. By so providing a distribution of transmission or reception gain in the lengthwise direction of the elements by forming the transducers, it is possible to maintain a good resolving power while improving the signal/noise ratio during transmission or reception. In that case, it is desirable with regard to the direction of row of the elements that a signal having both a phase distribution and distribution of transmission or reception gain be applied to each element in the sets of elements effecting transmission or reception. To realize this, attenuators corresponding to the number of elements in a set may be provided to have the transmission signal gain distribution and disposed in a delay circuit which is an electric circuit to be described, and also for reception each preamplifier 33 may be adjusted to provide a desired reception gain distribution.

Figure 13:
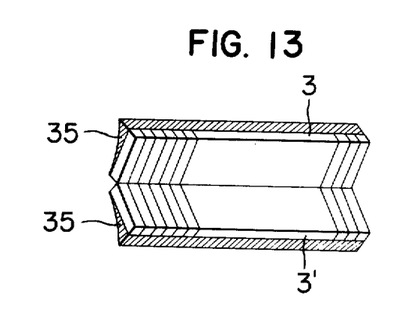

FIG. 13 shows a further embodiment of the present invention. This embodiment, like the previous embodiment, is such that the transducer has a distribution of transmission or reception gain of the acoustic wave in the lengthwise direction of the elements, and the elements are provided with backing layers 35 having a thickness distribution in the lengthwise direction of the elements. With regard to the direction of row of the elements, signals having both a phase distribution and a gain distribution may be applied to a set of elements, as already described in connection with the previous embodiment. By this, it is possible to suppress the side lobe in the transmission and the reception sensitivity characteristics of the acoustic wave and accordingly, to realize a good signal/noise ratio as well as a good azimuthal resolving power.

Figure 15:
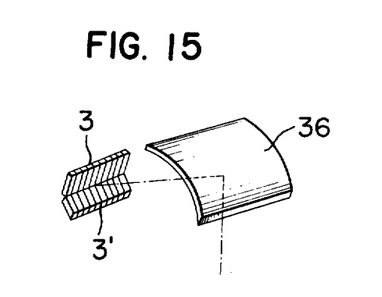

The foregoing embodiments have been described by supposing that the acoustic wave fronts from each set are restricted to plane waves. However, with the plane waves the region in which the wave fronts overlap each other on the axis 14 is determined by the obtuse angle between the plane waves and also by the lateral dimension of the plane waves. Therefore, where a large or a small region is desired, the acoustic wave fronts from each set should have a predetermined curved surface. For example, in order that the acoustic wave fronts may have a spherical surface, such may be accomplished by imparting delay distribution to the operation of the two-dimensional transducer array as shown in FIG. 7, whereas this is not possible with one-dimensional array. FIG. 14 shows an embodiment in which the transducer itself is curved in a direction perpendicular to the scanning direction to thereby provide wave front having a curved surface. FIG. 15 shows an embodiment in which an acoustical optical element such as a concave mirror 36 curved only in a direction orthogonal to the scanning direction is disposed in the path of the plate wave from each set to thereby transform its plane wave front into a curved surface.

Description will now be made of electric circuits used in these embodiments. These electric circuits may be readily modified in accordance with the intended purpose of one skilled in the art of the electric circuit in the electronic focusing type scanner. Therefore, the electric circuit in each embodiment need not be described, but description will be made only of the electric circuit in the embodiment of FIG. 9.

Figure 16:
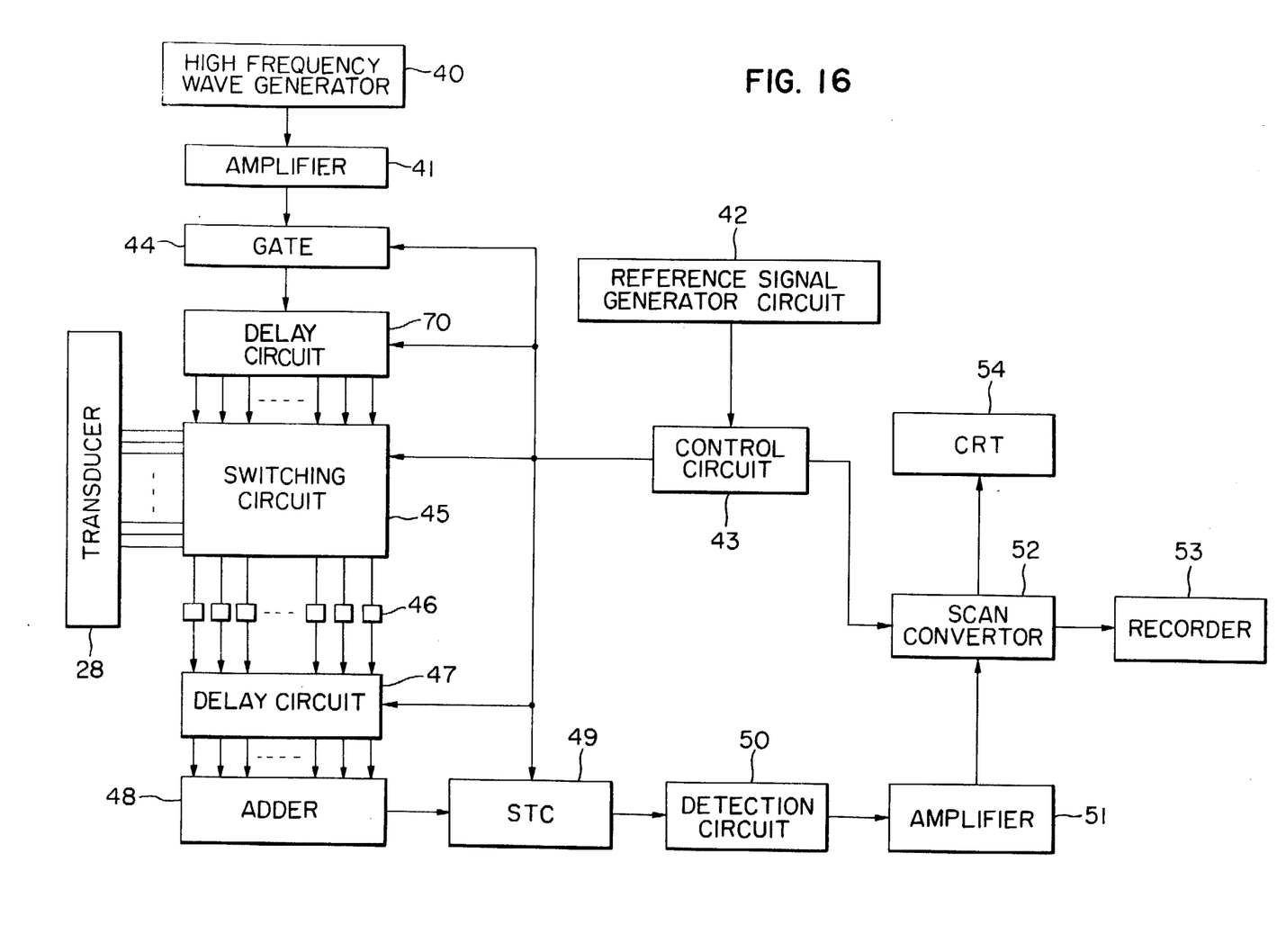
FIG. 16 is a block diagram of the electric circuit usable in any of the embodiments of the present invention.

Referring to FIG. 16, a high frequency signal generated by an oscillator 40 is amplified by an amplifier 41. On the other hand, a signal generated by a reference signal generating circuit 42 is applied as input to a control circuit 43, which drives a gate 44 which in turn modulates the signal from the amplifier 41 into a pulse wave to be applied to the transducer elements. This pulse wave is passed through a delay circuit 70 controlled by the control circuit 43 and further, by a switching circuit 45 controlled by the control circuit 43, a transmission signal is imparted so that the predetermined phase distribution of the transmission signal corresponds to the set of elements in the transducer which is used at the right desired moment. The preamplifiers differing in amplification factor may be disposed in the delay circuit to impart a gain distribution to the transducer elements. The acoustic waves reflected from an object are received by transducer elements and passed through the switching circuit 45 for amplification by preamplifiers 46 connected to the individual elements forming the set now in use, thereby providing amplified electrical reception signals. These reception signals are given the predetermined phase distribution by a delay circuit 47 controlled by the control circuit 43, whereafter they are added together by a circuit 48. The preamplifiers 46 may differ in amplification factor to impart the gain distribution to the signals received by transducer elements.

Designated by 49 is an STC (sensitivity time control) circuit controlled by the control circuit 43, and the output of the STC circuit enters a detection circuit 50.

The signals from the detection circuit pass through an amplifier 51 to a scan-converter 52 controlled by the control circuit. The signals from the scan-converter 52 are applied to a recorder 53 and to a display unit 54 such as CRT (cathode ray tube) which receives the scanning signals from the control circuit, whereby the signals are recorded and displayed respectively.

Further explaining the function of the structure of FIG. 16, block circuit is used for controlling the transducer of FIG. 9 wherein the transducer arrays 22 and 23 are in group construction. First pulse actuation, second pulse actuation . . . Nth pulse actuation are effected sequentially. Each of the group consists of eight elements. For example, group 24 consists of the first - eighth elements, from the left, of the array 22; similarly group 25 consists of 9th-16th elements; group 26 of the array 23 consists of 1st-8th elements; and group 27 consists of 9th-16th elements. In the second actuation, group 24 consists of 2-nd-9th elements of array 22; group 25 consists of 10th-17th elements; group 26 consists of 2nd-9th elements of array 23; the group 27 consists of 10th-17th elements. If the number of the pulse actuation of the transducer is N, then in the Nth pulse actuation, the group 24 consists of Nth−(N+7)th elements of array 22; group 25 consists of (N+8)th−(N+15)th elements; group 26 consists of Nth−(N+7)th elements of array 23; and group 27 consists of (N+8)th+(N+15)th elements. Elements of each of the groups are actuated sequentially in the direction arrayed. The axis 14 is at the right middle of the groups 24, 25, 26 and 27. In the Figure, the axis 16 is between 8th element and 9th element at the junction between array 22 and array 23. The axis 14 moves by the amount of a single element every time of the pulse actuation. The grouping of the elements is effected by the switching circuit shown in FIG. 16. The switching circuit 45 determines, in accordance with the signal from the control circuit 43, which element should receive the signal which is given the phase distribution by the delay circuit 70, thus grouping the elements.

Figure 17:
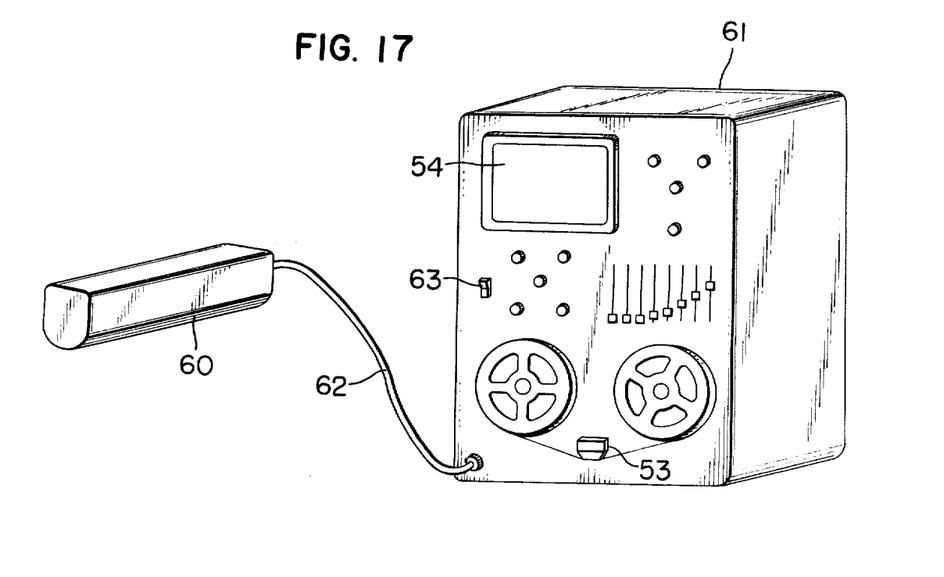
FIG. 17 is a pictorial perspective view of the apparatus shown in FIG. 16.

FIG. 17 shows a pictorial perspective view of the FIG. 16 apparatus which includes a head portion 60 and a main body 61. The transducer is disposed in the head portion 60, and the other parts are disposed in the main body 61. On the front face of the main body, there are disposed a display unit 54, a recorder 53, a power switch 63 and various controllers.

What I claim is:

1. An apparatus for scanning acoustic waves in accordance with movement of a presumed axis moved on a certain surface, said apparatus comprising an acoustic transducer element row comprising a plurality of acoustic transducer elements; a pulse signal generating circuit for imparting energy to individual ones of said acoustic transducer elements; and operation controller means for controlling the operations of individual ones of said acoustic transducer elements; said operation controller having the function of causing individual ones of said acoustic transducer elements to operate as a plurality of sets, each including a plurality of acoustic transducer elements, in accordance with the position to which said presumed axis is moved each time said pulse signal is obtained and the function of imparting an operation time difference to the acoustic transducer elements in each of said sets so that the envelope surface of wave fronts formed by the individual acoustic elements forming at least one of said sets and the envelope surface of wave fronts formed by the individual acoustic elements forming at least one of the other sets overlap each other on said presumed axis and the point of overlap between said wave fronts is moved along said presumed axis, and that the center of curvature of the envelope surface formed by each of said sets lies outside said presumed axis.

2. An apparatus according to claim 1, wherein said acoustic transducer elements are elements having a gain distribution of acoustic wave transmission in a direction perpendicular to the direction of said row.

3. An apparatus according to claim 1, wherein said plurality of acoustic transducer elements are connected to an electric circuit imparting a gain distribution in the direction of said row.

4. An apparatus according to claim 1, wherein said acoustic transducer row comprises a plurality of units formed by a plurality of elements and disposed in the direction of said element row.

5. An acoustic wave scanning apparatus for detecting acoustic waves from each point on a presumed axis moved on a certain surface, said apparatus comprising an acoustic transducer row comprising a plurality of acoustic transducer elements; and controller means for controlling the reception time of individual ones of said acoustic transducer elements; said controller means having the function of causing individual ones of said acoustic transducer elements to operate as a plurality of sets, each including a plurality of acoustic elements, in accordance with the position to which said presumed axis is moved each time receiving signal is obtained and the function of effectively causing the wave front made of acoustic waves simultaneously received by individual ones of the acoustic transducer elements forming at least one of said sets to overlap the wave fronts made of acoustic waves simultaneously received by individual ones of the acoustic transducer elements forming at least one of the other sets and the function of operating said sets so that the point of overlap between said wave fronts is moved along said presumed axis and that said sets receive such wave fronts whose centers of curvature lie outside said presumed axis.

6. An apparatus according to claim 5, wherein said acoustic transducer elements are elements having a gain distribution of acoustic wave reception in a direction perpendicular to the direction of said row.

7. An apparatus according to claim 5, wherein said plurality of acoustic transducer elements are connected to an electric circuit imparting a gain distribution in the direction of said row.

8. An apparatus according to claim 5, wherein said acoustic transducer row comprises a plurality of units formed by a plurality of elements and disposed in the direction of said element row.

9. An apparatus for scanning acoustic waves in accordance with the movement of a presumed axis moved on a certain surface, said apparatus comprising a plurality of acoustic transducer element rows each comprising a plurality of acoustic transducer elements; a pulse signal generating circuit for imparting energy to individual one of said acoustic transducer element; and an operation controller means for controlling the operations of individual ones of said acoustic transducer elements; said operation controller means having the function of causing individual ones of the acoustic transducer elements to operate as a plurality of sets for each of said rows in accordance with the position to which said presumed axis is moved each time said pulse signal is obtained and the function of causing the envelope surface formed by acoustic waves from individual ones of the acoustic transducer element forming at least one of said sets to overlap the envelope surface of the wave fronts formed by acoustic waves from individual ones of the acoustic transducer elements forming at least one of the other sets and the function of imparting an operation time difference to the acoustic transducer elements in each of said sets so that the point of overlap between said envelope surfaces moves along said presumed axis and that the center of curvature of the envelope surface formed by each of said sets lies outside said presumed axis.

10. An apparatus for detecting acoustic waves from each point on a presumed axis moving on a surface, said apparatus comprising a plurality of acoustic transducer element rows each comprising a plurality of acoustic transducer elements; and an operation controller means for controlling the reception time of individual ones of said acoustic transducer elements, said operation controller means having the function of causing individual ones of the acoustic transducer elements to operate as a plurality of sets for each of said rows in accordance with the position to which said presumed axis is moved each time receiving signal is obtained and the function of effectively causing the wave fronts made of acoustic waves received simultaneously by individual ones of the acoustic transducer elements forming at least one of said sets to overlap wave front made of acoustic waves simultaneously received by at least one of the other sets of acoustic transducer elements and the function of operating the sets so that the point of overlap between said wave fronts moves along said presumed axis and that they receive such wave fronts whose centers of curvature lie outside said presumed axis.

11. An apparatus for scanning acoustic waves in accordance with movement of a presumed axis moved on a certain surface, said apparatus comprising a plurality of acoustic transducer element rows each comprising a plurality of acoustic transducer elements each having a plane surface of arranged elements; said surface of element rows making an angle therebetween; and operation controller means for controlling the operation of individual ones of said acoustic transducer elements; said operation controller means having the function of causing individual ones of the acoustic transducer elements to operate as a plurality of sets for each of said rows in accordance with the position to which said presumed axis is moved each time receiving signal is obtained and the function of causing the envelope surface of wave fronts formed by acoustic waves from at least one of said sets to overlap the envelope surface of wave fronts formed by acoustic waves from at least one of the other sets and the function of imparting an operation time difference to the acoustic transducer elements in each of said sets so that the point of overlap between said envelope surfaces moves along said presumed axis and that the center of curvature of the envelope surface formed by each of said sets lies outside said presumed axis.

12. An apparatus according to claim 11, wherein said surfaces of arranged elements are curved.

13. An apparatus according to claim 11, wherein acoustical optical elements are disposed in the paths of the acoustic waves from each of said sets.

14. An apparatus for detecting acoustic waves from each point on a presumed axis moving on a certain surface, said apparatus comprising a plurality of acoustic transducer element rows each comprising a plurality of acoustic transducer elements, each having a plane surface of arranged elements, said surface of element rows making an angle therebetween; and operation controller means for controlling the reception time of individual ones of said acoustic transducer elements; said operation controller means having the function of causing in individual ones of the acoustic transducer elements to operate as a plurality of sets for each of said rows in accordance with the position to which said presumed axis is moved each time receiving signal is obtained and the function of causing effectively the wave front made of acoustic waves simultaneously received by individual ones of the acoustic transducer elements forming at least one of said sets to overlap the wave front made of acoustic waves simultaneously received by at least one of the other set of acoustic transducer elements and the function of operating the acoustic transducer elements so that the point of overlap between said wave fronts moves along said presumed axis and that they receive such wave fronts whose centers of curvature lie outside said presumed axis.

15. An apparatus according to claim 14, wherein said surfaces of arranged elements are curved.

16. An apparatus according to claim 15, wherein acoustical optical elements are disposed in the paths of the acoustic waves from each of said sets.

17. An apparatus for scanning acoustic waves in accordance with movement of a presumed axis moving on a certain surface, said apparatus comprising a plurality of acoustic transducer element rows each comprising a plurality of acoustic transducer elements, each having a plane surface of arranged element, said surface of element rows making an angle therebetween; a pulse signal generating circuit for imparting energy to individual ones of said acoustic transducer element; and operation controller means for controlling the operations of individual ones of said acoustic transducer elements; said operation controller means having the function of causing individual ones of the acoustic transducer elements to operate as a plurality of sets for each of said rows in accordance with the position to which said presumed axis is moved each time receiving signal is obtained and the function of causing the envelope surface of wave fronts formed by acoustic waves from at least one of said sets to overlap the envelope surface of wave fronts formed by acoustic waves from at least one of the other sets and the function of imparting an operation time difference to the acoustic transducer elements in each of said sets so that the point of overlap between said envelope surfaces moves along said presumed axis and that the center of curvature of the envelope surface formed by acoustic waves from each of said sets lies outside said presumed axis.

18. An apparatus for scanning acoustic waves from each point on a presumed axis moving on a certain surface, said apparatus comprising a plurality of acoustic transducer element rows each comprising a plurality of acoustic transducer elements, each having a plane surface of arranged elements, said surface of element rows making an angle therebetween; and operation controller means for controlling the reception time of individual ones of said acoustic transducer elements; said operation controller means having the function of causing individual ones of the acoustic transducer elements to operate as a plurality of sets for each of said rows in accordance with the position to which said presumed axis is moved each time receiving signal is obtained and the function of effectively causing the wave front made of acoustic waves simultaneously received by individual ones of the acoustic transducer elements forming at least one of said sets to overlap the wave front made of acoustic waves simultaneously received by at least one of the other sets of acoustic transducer elements and the function of operating the acoustic transducer elements so that the point of overlap between said wave fronts moves along said presumed axis and that they receive such wave fronts whose centers of curvature lie outside said presumed axis.

* * * * *